United States Patent [19]

Jäger et al.

[11] 4,291,044
[45] Sep. 22, 1981

[54] COMBATING FUNGI WITH 1-(AZOL-1-YL)-2-SUBSTITUTED-ALKEN-3-ONES

[75] Inventors: Gerhard Jäger; Udo Kraatz, both of Leverkusen; Karl H. Büchel, Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 84,208

[22] Filed: Oct. 12, 1979

[30] Foreign Application Priority Data

Oct. 28, 1978 [DE] Fed. Rep. of Germany ....... 2846980

[51] Int. Cl.³ .................... A01N 43/50; A01N 43/64; C07D 233/60; C07D 249/08
[52] U.S. Cl. .................................. 424/269; 424/232; 424/245; 424/273 R; 542/413; 542/426; 542/427; 542/440; 542/458; 548/101; 548/262; 548/341
[58] Field of Search ............... 542/413, 426, 427, 440, 542/458; 548/101, 262, 341; 424/245, 269, 273 R

[56] References Cited

U.S. PATENT DOCUMENTS 3,940,413  2/1976  Kramer et al. ....................... 548/341
3,974,174  8/1976  Buchel et al. ....................... 424/269
4,005,083  1/1977  Buchel et al. ....................... 424/269
4,130,409  12/1978  Shephard et al. .................... 548/262

FOREIGN PATENT DOCUMENTS 2331  6/1979  European Pat. Off. ................ 71/92
3884  9/1979  European Pat. Off. ................ 71/92

Primary Examiner—Alton D. Rollins
Attorney, Agent, or Firm—Sprung, Felfe, Horn, Lynch & Kramer

[57] ABSTRACT

1-(Azol-1-yl)-2-substituted-alken-3-ones of the formula

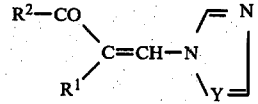

in which $R^1$ represents alkyl, alkoxy, alkylthio, alkylsulphonyl, alkylcarbonyl, optionally substituted phenyl, optionally substituted phenoxy, optionally substituted phenylthio, optionally substituted phenylsulphonyl or optionally substituted phenyl carbonyl, $R^2$ represents alkyl, cycloalkyl or optionally substituted phenyl and Y represents a nitrogen atom or the CH group.

12 Claims, No Drawings

COMBATING FUNGI WITH 1-(AZOL-1-YL)-2-SUBSTITUTED-ALKEN-3-ONES

The present invention relates to and has for its objects the provision of particular new 1-(azol-1-yl)-2-substituted-alken-3-ones which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

The present invention relates to certain new 1-etheneazole derivatives, to a process for their preparation and to their use as fungicides.

It has already been disclosed that certain 1-ethylimidazole and -triazole derivatives, for example 1-(imidazol-1-yl)- or 1-(1,2,4-triazol-1-yl)-1-phenoxy-4,4-dimethyl-pentan-3-ones which are substituted in the phenyl part, have good fungicidal properties (see U.S. Pat. Nos. 3,914,427 and 3,974,174). However, their action is not always completely satisfactory, especially when low amounts and concentrations are used.

The present invention now provides, as new compounds, the 1-ethylene-azole derivatives of the general formula

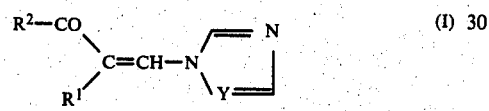

in which
R$^1$ represents alkyl, alkoxy, alkylthio, alkylsulphonyl, alkylcarbonyl, optionally substituted phenyl, optionally substituted phenoxy, optionally substituted phenylthio, optionally substituted phenylsulphonyl or optionally substituted phenylcarbonyl,
R$^2$ represents alkyl, cycloalkyl or optionally substituted phenyl and
Y represents a nitrogen atom or the CH group, and physiologically acceptable acid addition salts and metal complexes thereof.

Surprisingly, the compounds according to the invention exhibit a considerably higher fungicidal activity than 1-ethyl-imidazole and -triazole derivatives known from the state of the art, such as 1-(imidazol-1-yl)- and -(1,2,4-triazole-1-yl)-1-phenoxy-4,4-dimethyl-pentan-3-ones, substituted in the phenyl part, which are closely related compounds chemically and from the point of view of their action. The substances according to the invention thus represent an enrichment of the art.

Preferably, in formula (I), R$^1$ represents straight-chain or branched alkyl, alkoxy, alkylthio, alkylsulphonyl or alkylcarbonyl with in each case 1 to 4 carbon atoms in the alkyl part; or represents an optionally substituted phenyl, phenoxy, phenylthio, phenylsulphonyl or phenylcarbonyl radical, the substituent(s) being selected from halogen, straight-chain or branched alkyl with 1 to 4 carbon atoms, halogenoalkyl with 1 to 2 carbon atoms and 1 to 5 identical or different halogen atoms (especially fluorine and chlorine atoms) and phenyl which is itself optionally substituted by halogen; and
R$^2$ represents straight-chain or branched alkyl with 1 to 4 carbon atoms, cycloalkyl with 5 to 8 carbon atoms or optionally substituted phenyl, the substituent(s) being selected from halogen, straight-chain or branched alkyl with 1 to 4 carbon atoms, halogenoalkyl with 1 to 2 carbon atoms and 1 to 5 identical or different halogen atoms (especially fluorine and chlorine atoms) and phenyl which is itself optionally substituted by halogen.

The compounds of the formula (I) can exist in two geometric isomer forms, depending on the arrangement of the groups which are bonded to the carbon atoms linked by the double bond. The isomers and the mixtures thereof are encompassed by formula (I).

Those compounds of the formula (I) in which R$^1$ represents methyl, methoxy, methylthio, methylsulphonyl, acetyl, ethyl, isopropyl or tert.-butyl, or represents a phenyl, phenoxy, phenylthio, phenylsulphonyl or phenylcarbonyl radical which optionally may carry one or more substituents selected independently from fluorine, chlorine, bromine, methyl, ethyl and phenyl, and R$^2$ represents methyl, isopropyl, tert.-butyl or cyclohexyl, or represents phenyl which optionally may carry one or more substituents selected independently from fluorine, chlorine, bromine, methyl, ethyl and phenyl, are very particularly preferred.

The following compounds of the general formula (I) may be mentioned specifically, in addition to the compounds mentioned in the preparative examples later in this text:

| R$^1$ | R$^2$ | Y |
|---|---|---|
| CH$_3$ | (phenyl) | N or CH |
| C$_2$H$_5$ | (phenyl) | N or CH |
| i-C$_3$H$_7$ | (phenyl) | N or CH |
| t-C$_4$H$_9$ | (phenyl) | N or CH |
| CH$_3$ | (phenyl)–Cl | N or CH |
| CH$_3$ | Cl–(phenyl)–Cl | N or CH |
| CH$_3$O— | (phenyl) | N or CH |
| CH$_3$S— | (phenyl) | N or CH |
| CH$_3$SO$_2$— | (phenyl) | N or CH |
| CH$_3$CO— | (phenyl) | N or CH |
| (phenyl) | —(phenyl)—Cl | N |
| (phenyl) | Cl–(phenyl)—Cl | N or CH |

The invention also provides a process for the preparation of a 1-ethene-azole derivative of the formula (I) in which a 1-halogeno-ethene derivative of the general formula

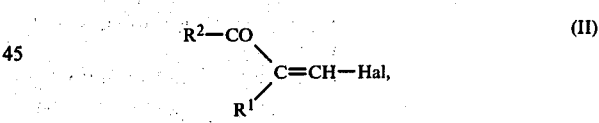

in which
R¹ and R² have the meanings stated above and Hal represents halogen,
is reacted with an alkali metal salt of an azole, of the general formula

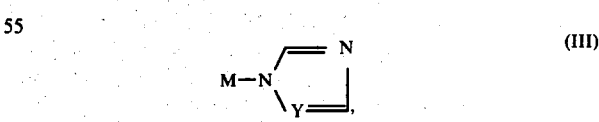

in which
Y has the meaning stated above and
M represents an alkali metal,
in the presence of a diluent.

Furthermore, the 1-ethene-azole derivatives of the formula (I) obtainable according to the invention can be converted into salts by reaction with acids, or into metal salt complexes by reaction with metal salts. In some cases, it proves advantageous to obtain the compounds of the formula (I) in the pure form via their salts.

If, for example, 1-chloro-2-(4-fluorophenoxy)-4,4-dimethyl-penten-3-one and sodium imidazole are used as starting substances, the course of the reaction can be represented by the following equation:

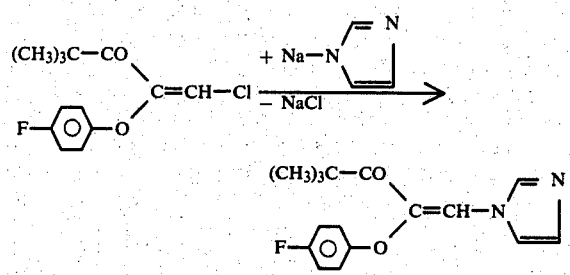

The formula (II) provides a general definition of the 1-halogeno-ethene derivatives to be used as starting substances for the process according to the invention.

In this formula, $R^1$ and $R^2$ preferably represent those radicals which have already been mentioned as preferred in the case of the compounds of the formula (I). Hal preferably represents chlorine or bromine.

1-Halogeno-ethene derivatives of the formula (II) are known and can all be obtained in a generally known manner when corresponding ethene derivatives of the general formula

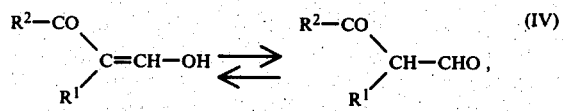

in which $R^1$ and $R^2$ have the meanings stated above, are reacted with a halogenating agent, such as phosphorus halides and sulphur halides (thionyl chloride, sulphuryl chloride, phosphorus trichloride or tribromide and phosphorus oxychloride may be mentioned as examples), if appropriate in the presence of a diluent, for example toluene or xylene, at temperatures between 20° and 100° C. (see also the preparative examples later in this text).

1-Halogen-ethene derivatives of the formula (IV) are known [see, inter alia, Liebigs Ann. Chem. 379, 230 (1911)] and can all be obtained in a generally known manner, by a process in which known ketones of the general formula

in which $R^1$ and $R^2$ have the meanings stated above, are reacted with formic acid esters of the general formula

in which $R^3$ represents methyl or ethyl, in the presence of sodium methylate or ethylate in methanol or ethanol respectively, at temperatures between 0° and 40° C. (see also the preparative examples).

The formula (III) provides a general definition of the alkali metal salts of azoles which are also to be used as starting substances for the process according to the invention. In this formula, Y has the meaning indicated in the definition of the compounds of this invention and M preferably represents sodium or potassium.

The alkali metal salts of azoles, of the formula (III), are known. They are obtained by reacting imidazole or 1,2,3-triazole with sodium methylate or potassium methylate in methanol, or by reacting imidazole with an equivalent amount of the corresponding alkali metal hydride.

Possible diluents for the reaction according to the invention are any of the inert organic solvents. These include, as preferences, nitriles, such as propionitrile, and in particular acetonitrile; ketones, such as diethyl ketone, and in particular acetone; aromatic hydrocarbons, such as benzene, toluene or xylene; halogenated hydrocarbons, such as chloroform or methylene chloride; and formamides, such as, in particular, dimethylformamide.

The reaction temperatures can be varied within a substantial range in carrying out the process according to the invention. In general, the reaction is carried out at from 0° to 150° C., preferably from 20° to 120° C.

Equimolar amounts of the reactants are preferably used in carrying out the process according to the invention. The compound of the formula (I) is isolated in the customary manner.

In general, in carrying out the process according to the invention, one isomer (cis or trans) is obtained in a larger amount than the other. If appropriate, the isomers can be separated by generally known methods, for example by gas/liquid chromatography. However, it can also be appropriate to use the isomer mixture as the active compound.

Any of the physiologically acceptable acids can be used for the preparation of acid addition salts of the compounds of the formula (I). These acids include, as preferences, hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicyclic acid, sorbic acid and lactic acid), and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiological acids. These include, as preferences, hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, the powedery mildew of cucumber causative organism (*Erysiphe cichoracearum*) or the powdery mildew of barley causative organism (*Erysiphe graminis*); for combating Venturia species, for example the apple scab causative organism (*Fusicladium dendriticum*), and for combating Puccinia species, for example the cereal rust causative organism (*Puccinia recondita*). Good actions are also achieved against *Pyricularia oryzae* and *Pellicularia sasakii* in rice.

When used in appropriate concentrations, the substances according to the invention also exhibit a growth-regulating action.

The active compounds can be converted into the customary formulations, such as solutions, emulsions, powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalene, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quarts, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They are used in the customary manner, for example by watering, immersion, spraying, atomizing, misting, vaporising, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, especially 0.01 to 10 g, are generally employed per kilogram of seed.

For the treatment of soil, active compound concentrations of, in general, 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

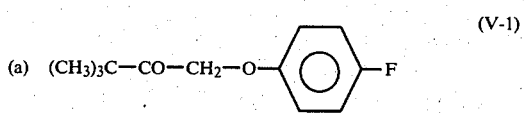
(a) $(CH_3)_3C-CO-CH_2-O-$⟨phenyl⟩$-F$  (V-1)

418.3 g (3.11 mol) of 2,2-dimethyl-4-chloro-butan-3-one were added dropwise to a suspension, heated to the boil, of 315 g (2.8 mol) of 4-fluorophenol and 386.4 g (2.8 mol) of potassium carbonate in 1,500 ml of acetone. The mixture was stirred under reflux for 4 hours. After cooling to room temperature, the salt which had separated out was filtered off and the filtrate was concentrated in vacuo. The oil which remained was distilled in vacuo. 101.5 g (86.2% of theory) of 2,2-dimethyl-4-(4-fluorophenoxy)-butan-3-one of boiling point 83°–84° C./0.05 mm Hg ($n_D^{20}=1.4919$) were obtained.

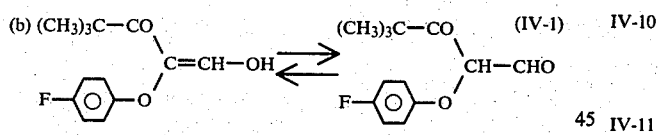
(b)  (IV-1)

163 g (2.2 mol) of formic acid ethyl ester were added dropwise to a solution of 136 g of sodium ethylate in 1,500 ml of ethanol at 0° C. 420 g (2 mol) of 2,2-dimethyl-4-(4-fluorophenoxy)-butan-3-one were then slowly stirred in at 0° C. After a reaction time of 24 hours at 0° C., the mixture was allowed to warm to room temperature and was subsequently stirred at this temperature for a further 96 hours. The reaction mixture was poured onto 5,000 ml of ice-water and the organic phase was separated off by extracting with chloroform. Unreacted starting material could be isolated from this chloroform solution and re-used. The aqueous phase was acidified with 10% strength hydrochloric acid, while cooling, and the oil which separated out was taken up in chloroform. The chloroform phase was dried over sodium sulphate and concentrated by distilling off the solvent in vacuo. The oil which remained was distilled in vacuo. 170 g (83% of theory, relative to unreacted product) of 1-hydroxy-2-(4-fluorophenoxy)-4,4-dimethyl-penten-3-one of boiling point 101°–102° C./0.6 mm Hg ($n_D^{20}=1.5132$) were obtained.

The following intermediates of the general formula

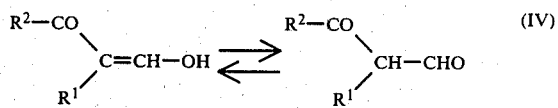
(IV)

were obtained by analogous procedures:

TABLE 1

| Intermediate No. | $R^1$ | $R^2$ | Boiling point (°C.)/mm Hg column. Melting point (°C.) |
|---|---|---|---|
| IV-2 | $-O-$⟨phenyl⟩$-Cl$ | $C(CH_3)_3$ | 112-13/0.15 |
| IV-3 | $-O-$⟨phenyl with Cl⟩$-Cl$ | " | Melting point 81–83 |
| IV-4 | $-O-$⟨phenyl⟩$-$⟨phenyl⟩ | " | Oil |
| IV-5 | $-O-$⟨phenyl⟩$-CH_3$ | " | Oil |
| IV-6 | $-O-$⟨phenyl with $CH_3$⟩ | " | Melting point 67–70 |
| IV-7 | $-O-$⟨phenyl with Cl⟩ | " | 101-03/0.1 |
| IV-8 | $-O-$⟨phenyl⟩ | " | 77-79/0.03 |
| IV-9 | $-O-$⟨phenyl with Cl, Cl⟩ | " | 117/0.07 |
| IV-10 | $-O-$⟨phenyl with Cl⟩ | " | 98-99/0.07 |
| IV-11 | ⟨phenyl⟩ | ⟨phenyl⟩ | Melting point 112-13 |
| IV-12 | ⟨phenyl⟩ | $Cl-$⟨phenyl⟩$-$ | Melting point 104-05 |

(c) (II-1)  $(CH_3)_3C-CO-C(=CH-Cl)-O-$⟨phenyl⟩$-F$ 297.5 g (2.5 mol) of thionyl chloride were stirred slowly into a solution, warmed to 60° C., of 404.6 g (1.7 mol) of 1-hydroxy-2-(4-fluorophenoxy)-4,4-dimethyl-penten-3-one in 3,000 ml of anhydrous toluene. The mixture was kept at the above temperature for 12 hours and then the solvent and excess thionyl chloride were distilled off. The oil which remained was distilled in vacuo. 353.3 g (81% of theory) of 1-chloro-2-(4-fluorophenoxy)-4,4-dimethyl-penten-3-one of boiling point 95°–103° C./0.3 mm Hg were obtained.

The following intermediates of the general formula

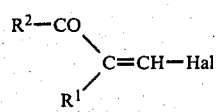

were obtained by an analogous procedure:

concentrated by distilling off the solvent in vacuo. 272.4 g (94.5% of theory) of crude 1-imidazol-1-yl)-2-(4-fluorophenoxy)-4,4-dimethyl-penten-3-one were obtained as a brown oil.

A solution of 52.5 ml of 96% strength nitric acid in 105 ml of chloroform was added to a solution of 252 g (0.874 mol) of the above oil in 315 ml of chloroform at

TABLE 2

| Intermediate No. | R¹ | R² | Hal | Boiling point (°C./mm Hg), Melting point °C. |
|---|---|---|---|---|
| II-2 | —O—⟨C₆H₄⟩—Cl | C(CH₃)₃ | Cl | 115–17/0.1 |
| II-3 | Cl-substituted —O—⟨C₆H₃⟩—Cl | " | " | 135–37/0.07 |
| II-4 | —O—⟨C₆H₄⟩—⟨C₆H₅⟩ | " | " | Oil |
| II-5 | —O—⟨C₆H₄⟩—CH₃ | " | " | 114–16/0.4 |
| II-6 | Cl-substituted —O—⟨C₆H₃⟩—CH₃ | " | " | 121–23/0.4 |
| II-7 | Cl-substituted —O—⟨C₆H₄⟩ | " | " | 107–10/0.15 |
| II-8 | —O—⟨C₆H₅⟩ | " | " | 98–100/0.25 |
| II-9 | Cl-substituted —O—⟨C₆H₃⟩—Cl | " | " | 132/0.3 |
| II-10 | —O—⟨C₆H₄⟩—Cl | " | " | 126–30/0.2 |
| II-11 | ⟨C₆H₅⟩ (stacked) | ⟨C₆H₅⟩ | " | Melting point 60–61 (pure isomer) |
| II-12 | ⟨C₆H₅⟩ (stacked) | Cl—⟨C₆H₄⟩— | " | Melting point 79–80 (pure isomer) |
| II-13 | ⟨C₆H₅⟩ | ⟨C₆H₅⟩ | " | 142–45/0.2 |

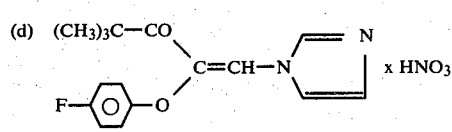

(d)    (1)

256.7 g (1 mol) of 1-chloro-2-(4-fluorophenoxy)-4,4-dimethyl-penten-3-one in 150 ml of acetonitrile were added dropwise to a suspension of 90 g (1 mol) of sodium imidazole, prepared from sodium methylate and imidazole in methanol, in 2,5000 ml of acetonitrile, while stirring. Thereafter, the reaction mixture was heated to the boil for 6 hours. It was allowed to cool to room temperature and was concentrated by distilling off the solvent in vacuo. The residue was taken up in 1,000 ml of ethyl acetate, the ethyl acetate mixture was washed three times with 200 ml of water each time and the organic phase was dried over sodium sulphate and 10° to 20° C., while stirring and cooling with ice. 860 ml of diethyl ether were then slowly added to the clear solution. 194.5 g (63.3% of theory) of 1-(imidazol-1-yl)-2-(4-fluorophenoxy)-4,4-dimethyl-penten-3-one nitrate of melting point 132°–133° C. (decomposition) were obtained.

EXAMPLE 2

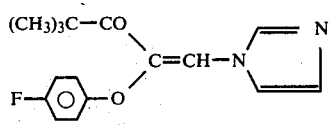

(2)

20 g (0.057 mol) of 1-(imidazol-1-yl)-2-(4-fluorophenoxy)-4,4-dimethyl-penten-3-one nitrate (obtained according to Example 1) were suspended in water. The suspension was rendered alkaline with 10% strength sodium carbonate solution. Extraction of the aqueous alkaline phase with chloroform gave, by customary methods of working up, 16.4 g (100% of theory) of 1-(imidazol-1-yl)-2-(4-fluorophenoxy)-4,4-dimethyl-penten-3-one of refractive index $n_D^{20}=1.5590$.

The following compounds of the general formula

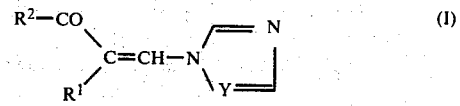

were obtained in a manner analogous to that described in Example 1 or 2:

TABLE 3

| Compound No. | R¹ | R² | Y | Melting point °C. |
|---|---|---|---|---|
| 3 | —O—⟨phenyl⟩—Cl | C(CH₃)₃ | CH | 93–4 |
| 4 | —O—⟨phenyl(2-Cl)⟩—Cl | " | " | 98–9 |
| 5 | —O—⟨phenyl⟩—⟨phenyl⟩ | " | " | 117–18 |
| 6 | —O—⟨phenyl⟩—CH₃ | " | " | 104–05 |
| 7 | —O—⟨phenyl⟩—⟨phenyl⟩ | " | " | 164 (decomposition) (xHNO₃) |
| 8 | —O—⟨phenyl⟩—CH₃ | " | " | 145 (decomposition) (xHNO₃) |
| 9 | —O—⟨phenyl(2-Cl)⟩—Cl | " | " | 132 (decomposition) (xHNO₃) |
| 10 | —O—⟨phenyl⟩—Cl | " | " | 144 (decomposition) (xHNO₃) |
| 11 | —O—⟨phenyl(2-Cl, 4-CH₃)⟩ | " | " | 128–29 |
| 12 | —O—⟨phenyl(2-Cl, 4-CH₃)⟩ | " | " | 153 (decomposition) (xHNO₃) |
| 13 | —O—⟨phenyl(2-Cl, 4-CH₃)⟩ | " | " | 250–252 (decomposition) (xHNO₃) |
| 14 | —O—⟨phenyl(2-Cl)⟩ | " | " | 115–16 |
| 15 | —O—⟨phenyl⟩ | " | " | 110–11 |
| 16 | —O—⟨phenyl(2-Cl)⟩ | " | " | 145 (decomposition) (xHNO₃) |
| 17 | —O—⟨phenyl⟩ | " | " | 202–05 (xHCl) |
| 18 | —O—⟨phenyl⟩ | " | " | 140 (decomposition) (xHNO₃) |
| 19 | —O—⟨phenyl(3-Cl)⟩ | " | " | 123 (decomposition) (xHNO₃) |

TABLE 3-continued
| Compound No. | R¹ | R² | Y | Melting point °C. |
|---|---|---|---|---|
| 20 | 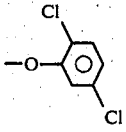 | " | " | 152 (decomposition) (xHNO₃) |
| 21 | 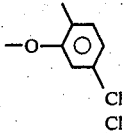 | " | " | 115–117 |
| 22 | 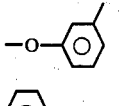 | " | " | 84–5 |
| 23 | 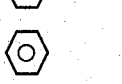 |  | " | 116–17 |
| 24 | 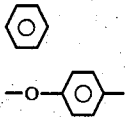 |  | " | 157 (decomposition) (xHNO₃) |
| 25 | 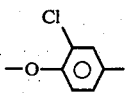 |  | N | 157–58 |
| 26 | 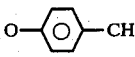 | C(CH₃)₃ | " | 87–8 |
| 27 |  | " | " | 117–18 |
| 28 | 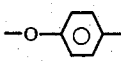 | " | " | 74–5 |
| 29 |  | " | " | 166–67 |
| 30 | 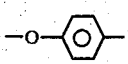 | " | " | 113 (decomposition) (xHNO₃) |
| 31 |  | " | " | $n_D^{20} = 1.5460$ |
| 32 | 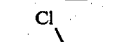 | " | " | 104–07 (xHNO₃) |
| 33 | 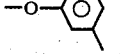 | " | " | 95–8 |
| 34 | 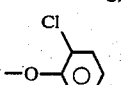 | " | " | 94–5 |
| 35 |  | " | " | 103 (decomposition) (xHNO₃) |
| 36 | 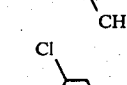 | " | " | 126–28 |
| 37 |  | " | " | 103 (decomposition) (xHNO₃) |
| 38 | 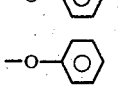 | " | " | 120–22 |

TABLE 3-continued

| Compound No. | R¹ | R² | Y | Melting point °C. |
|---|---|---|---|---|
| 39 | —O—⟨C₆H₄⟩—Cl (2-Cl) | " | " | 52-3 |
| 40 | —O—⟨C₆H₃(Cl)⟩—F | " | CH | 127 (decomposition) (xHNO₃) |
| 41 | —O—⟨C₆H₃(Br)⟩—F | " | " | 124 (decomposition) (xHNO₃) |
| 42 | —O—⟨C₆H₄⟩—NO₂ | " | N | 98-100 |
| 43 | —O—⟨C₆H₃(CH₃)⟩—CH₃ | " | CH | 119-20 |
| 44 | —O—⟨C₆H₃(CH₃)⟩—CH₃ | " | N | 86-88 |
| 45 | —O—⟨C₆H₄(CH₃)⟩ | " | CH | 110-11 |
| 46 | —O—⟨C₆H₄(CH₃)⟩ | " | N | 87-88 |
| 47 | —O—⟨C₆H₃(CH₃)⟩—Cl | " | CH | 111-12 |
| 48 | —O—⟨C₆H₃(CH₃)⟩—Cl | " | N | 98-100 |
| 49 | —O—⟨C₆H₃(CH₃)⟩—Cl | " | CH | 146-47 |
| 50 | —O—⟨C₆H₃(CH₃)⟩—Cl | " | N | 113-16 |

The fungicidal activity of the compounds of this invention is illustrated by the following examples wherein the compounds according to the present invention are each identified by the number (given in brackets) from Examples 1 and 2 hereinabove.

EXAMPLE 3

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21-22 deg. C. and 80-90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound the lower was the degree of mildew infection.

In this test, for example, the following compounds showed a very good action, which was superior to that of the compounds known from the prior art: (3), (4), (1) and (10).

EXAMPLE 4

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20 deg. C. and 100% relative atmospheric humidity.

After 10 days' dwell time of the plants at a temperature of 20 deg. C. and 80-90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

In this test for example, the following compounds showed a very good action, which was superior to that of the compounds known from the prior art: (3), (4), (27) and (5).

EXAMPLE 5

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18-20 degrees C. at a relative atmosphere humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

In this test, for example, the following compounds showed a very good action which was superior to that of the compounds known from the prior art: (3), (26), (4), (27) and (29).

EXAMPLE 6

Erysiphe test (cucumber)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23-24 degrees C. and at a relative atmospheric humidity of about 75%.

After 12 days, the infection of the cucumber plants was determined. The assessment data were converted to percent infection. 0% meant no infection; 100% meant that the plants were totally infected.

In this test, for example, the following compounds showed a very good action, which was superior to that of the compounds known from the prior art: (26), (27) and (1).

It will be appreciated that the instant specification and examples are set forth by way of illustration and not limitation, and that various modifications and changes may be made without departing from the spirit and scope of the present invention.

What is claimed is:

1. A 1-(azol-1-yl)-2-substituted-alken-3-one of the formula

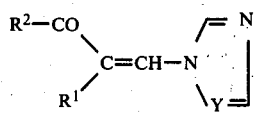

in which $R^1$ is phenoxy optionally substituted by halogen, alkyl with 1 to 4 carbon atoms, halogenoalkyl with 1 to 2 carbon atoms and 1 to 5 halogen atoms, phenyl or halophenyl, and $R^2$ is alkyl with 1 to 4 carbon atoms, cycloalkyl with 5 to 8 carbon atoms, phenyl, or phenyl substituted with halogen, alkyl with 1 to 4 carbon atoms, haloalkyl with 1 to 2 carbon atoms and 1 to 5 halogen atoms, phenyl or halophenyl, and Y is a nitrogen atom or the CH group,
or an addition product thereof with an acid or a metal salt.

2. A compound according to claim 1, in the form of an addition salt with an acid selected from hydrogen halide acids, phosphoric acid, nitric acid, sulphuric acid, monofunctional and bifunctional carboxylic and hydroxycarboxylic acids, and sulphonic acids.

3. A compound according to claim 1, in the form of a complex with a metal salt, the metal of which is copper, zinc, manganese, magnesium, tin, iron or nickel and the anion of which is halide, phosphate, nitrate or sulphate.

4. A fungicidal composition containing as active ingredient a fungicidally effective amount of a compound according to claim 1 in admixture with a diluent.

5. A method of combating fungi which comprises applying to the fungi, or to a habitat thereof, a fungicidally effective amount of a compound according to claim 1.

6. A method according to claim 5, in which the active compound is applied to seed, soil or a plant.

7. A compound according to claim 1, wherein such compound is

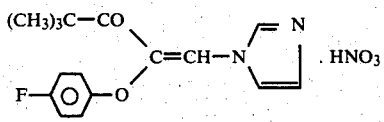
8. A compound according to claim 1, wherein such compound is
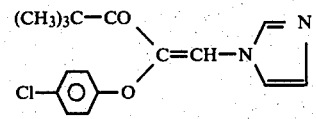
9. A compound according to claim 1, wherein such compound is
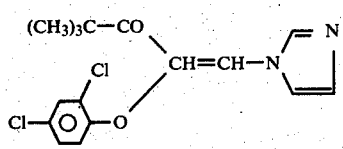
10. A compound according to claim 1, wherein such compound is
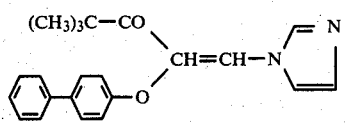
11. A compound according to claim 1, wherein such compound is
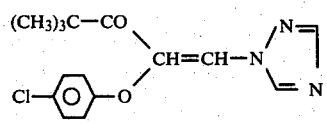
12. A compound according to claim 1, wherein such compound is
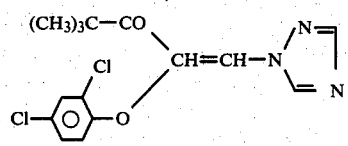
* * * * *